United States Patent [19]

Moore

[11] Plant 4,158

[45] Nov. 29, 1977

[54] MINIATURE ROSE PLANT

[76] Inventor: Ralph S. Moore, 2519 E. Noble Ave., Visalia, Calif. 93277

[21] Appl. No.: 737,410

[22] Filed: Nov. 1, 1976

[51] Int. Cl.[2] ..... A01H 5/00

[52] U.S. Cl. ..... Plt./9

[58] Field of Search ..... Plt./7, 9

*Primary Examiner*—Robert E. Bagwill

[57] ABSTRACT

A new and distinct variety of miniature rose having small, very double, light pink flowers which are profusely borne in small clusters on a small plant having small, disease resistant leaves.

1 Drawing Figure

1

The present invention relates to a new and distinct variety of hardy, dwarf, bush type rose plant of the miniature class; the variety being primarily characterized — as to novelty — by light pink buds and flowers which in general color effect are similar to June Time (miniature — U.S. Plant Pat. No. 2,563).

The variety is further characterized by:

An abundance of bloom with flowers usually borne several to the stem in loose cluster or spray.

Light fragrance.

A plant which is vigorous, of very bushy rounded shape and with semi-glossy small pointed leaflets; the buds and flowers being similar in form and size to Cinderella (miniature — U.S. Plant Pat. No. 1,051, expired).

The plant, which has a normal height of 10–12 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross of Ellen Poulsen (floribunda — not patented) as the seed parent and Fairy Princess (miniature — not patented) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers. Referring now specifically to the new and distinct variety of miniature rose plant, the following is a detailed description thereof in outline; all major color plate identification being by reference to the British Colour Council Horticultural Colour Chart, except where common terms of color definition are employed.

Type: Hardy, dwarf, bushy, seedling, greenhouse, outdoors; cut flowers; garden decoration; potted plant.

Class: Miniature. Variety name: 'Stacey Sue'.

Flowers borne: Singly but usually several together (three to five or more) on sturdy, wirey, short to medium length stems.

Flowers:

*Continuity.*—Continuous — repeat bloom all season.

*Fragrance.*—Light; sweet.

2

Quantity of bloom: Abundant, both outside and in greenhouse.

Bud:

*Peduncle.*—Medium length; slender but sturdy; erect; medium green, sometimes tinted bronze (outdoors); hairs — usually none.

*Before calyx breaks.*—Size — small. Form: medium long; pointed, with few foliaceous appendages and few or no hairs on surface of bud; with foliaceous parts extending beyond the tip of the bud equal to less than one-half of its length. Color — medium green, occasionally tinted with bronze (outdoors).

*As calyx breaks.*—Color — medium to light pink; opens same general color or lighter shade. Size — small.

Bloom:

*Size when fully open.*—Small, averaging about 25 to 27 mm.

*Petalage.*—Double 50 to 70 petals, arranged regularly — plus may have several small petaloids.

*Form.*—Full; rounded center at first, becoming more open in the center, with petals rolled loosely outward. Open flowers, at times, may show yellow stamens.

Petals: Medium thick; satiny on inside and on outside surfaces.

*Shape.*—Outside petals: broad lanceolate with rounded tip; intermediate — broad lanceolate with acute or rounded tip; inside — lanceolate to narrow lanceolate with acute tip.

Color: Newly opened flower from plant grown in plastic greenhouse (fall 1976), Visalia, Calif.

*Outside petal.*—Outside surface — may vary, near Fuchsine Pink 627/2 to Fuchsine Pink 627/3 — with both lighter and darker areas — and with small near white area at base. Inside surface — Fuchsine Pink 627/2 to Fuchsine Pink 627/3, similar to outside surface, shading into near-white at base.

*Intermediate petal.*—Outside surface — similar to outside petal. Inside surface — similar to outside petal.

*Inner petal.*—Outside surface — same as intermediate petal; inside surface — same as intermediate petal. General color effect newly opened flowers — light to medium pink, somewhat depending on the weather and time of year. Three days open: color similar to newly opened flowers but may be lighter shade. Behavior — opens well in all weather. Spent petals drop off. Flower longevity (September, 1976) — plant in pot 5-7 days or longer. Cut flowers at living room temperature — 3 to 5 days.

Reproductive organs:

*Stamens.*—Few (to none), arranged regularly around pistil.

*Filaments.*—Short, varying length, light yellow.

*Anthers.*—Some — usually well formed; yellow.

*Pollen.*—Scarce.

*Pistils.*—Average number.

*Styles.*—Fairly even; quite short; bunched; color — greenish.

*Stigma.*—Greenish.

*Ovaries.*—All enclosed in calyx.

*Hips.*—Few or none.

*Sepals.*—Permanent; spear shaped; recurved.

*Seeds.*—Few or none.

Foliage:

*Leaves.*—Compound of five (often seven) leaflets; abundant; small; soft to light leathery; semi-glossy.

*Leaflets.*—Shape: base rounded or rounded acute. Margin serrate.

*Color.*—Medium green; new growth — sometimes reddish.

*Rachis.*—Medium strength; upper side may have a few short tiny hairs and/or prickles, grooved; underside — several thorns and several hairs or tiny prickles.

*Stipules.*—Medium long; narrow to medium width; medium length narrow points which turn out usually at about 45 degrees or less.

Growth:

*Habit.*—Dwarf; bushy; rounded; much branched.

*Growth.*—Free; vigorous.

*Canes.*—Medium; slender; medium green.

*Main stems.*—Color; medium green.

*Thorns.*—Several, slender; slightly curved, inclined slightly downward; color — brown. Prickles — none. Hairs — none.

*Branches.*—Color: medium green. Thorns; several; medium length; slender; nearly straight — inclined slightly downward. Medium to short oval base. Prickles: none. Hairs: none.

*New shoots.*—Color: green but often slightly reddish. Thorns: several; color — brownish; slightly curved. Prickles — none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, essentially as illustrated and described, characterized by buds and flowers of a light to medium pink color resembling the June Time miniature rose (U.S. Plant Pat. No. 2,563) — and resembling the Cinderella miniature rose (U.S. Plant Pat. No. 1,051 — expired) in size and form of bud and flower; and further characterized by a plant which is vigorous and compact, said plant being easy to propagate from cuttings, with small, disease resistant, semi-glossy leaves, an abundance of bloom, making this variety useful as a potted plant, with flowers borne usually several to the stem in loose clusters.

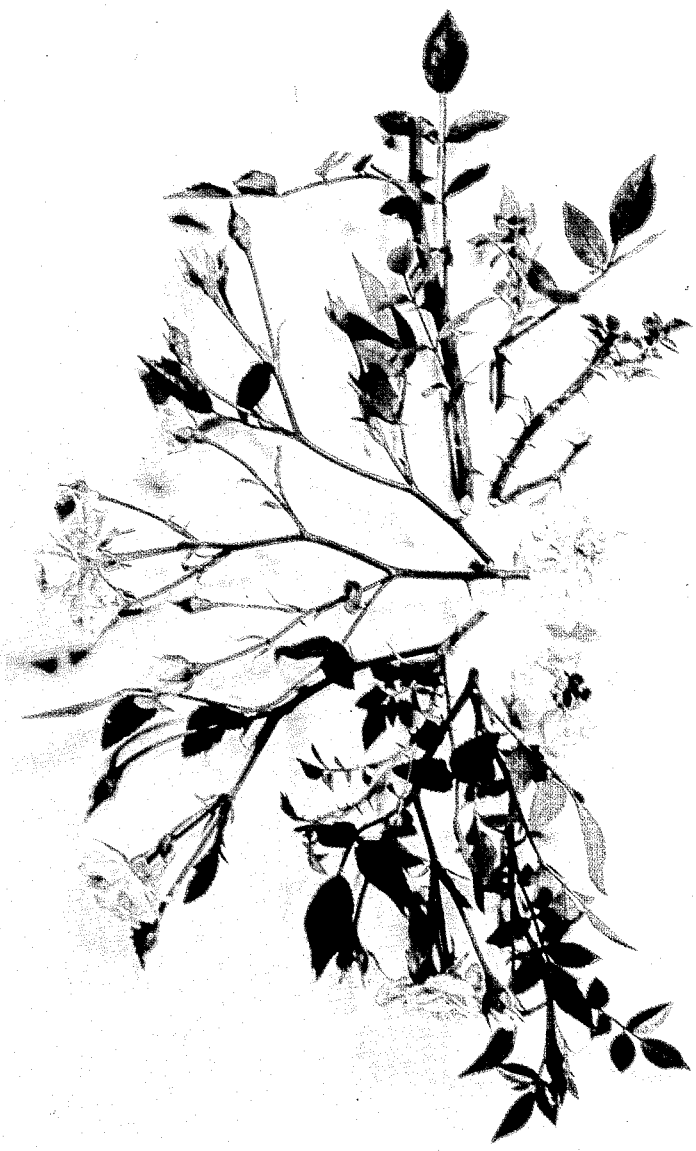

* * * * *